US006810679B2

(12) United States Patent
Odawara

(10) Patent No.: US 6,810,679 B2
(45) Date of Patent: Nov. 2, 2004

(54) COOLING APPARATUS AND SQUID MICROSCOPE USING SAME

(75) Inventor: Akikazu Odawara, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/367,139

(22) Filed: Feb. 14, 2003

(65) Prior Publication Data

US 2003/0172660 A1 Sep. 18, 2003

(30) Foreign Application Priority Data

Mar. 1, 2002 (JP) ........................................ 2002-055521

(51) Int. Cl.[7] .............................. F17C 13/02; F17C 9/02
(52) U.S. Cl. ........................................ 62/49.2; 62/50.2
(58) Field of Search ................................ 62/49.2, 50.2, 62/259.2

(56) References Cited

U.S. PATENT DOCUMENTS 3,092,974 A * 6/1963 Haumann et al. .............. 62/62
5,101,636 A * 4/1992 Lee et al. ..................... 62/48.1
5,506,200 A * 4/1996 Hirschkoff et al. .......... 505/162
5,834,938 A * 11/1998 Odawara et al. ............. 324/248
6,332,324 B1 * 12/2001 Saho et al. ................... 62/51.1
6,583,619 B2 * 6/2003 Zimmermann et al. ...... 324/248

* cited by examiner

Primary Examiner—William C. Doerrler
(74) Attorney, Agent, or Firm—Adams & Wilks

(57) ABSTRACT

A cooling apparatus has a storage vessel for storing a liquefied gas and an evaporated gas produced by evaporation of the liquefied gas, a cooling head cooled by the evaporated gas to approximately a boiling temperature of the liquefied gas, piping for conveying the evaporated gas from the storage vessel to the cooling head, and a gas collection port provided at one end portion of the piping above a liquid level of the liquefied gas for collecting only the evaporated gas from the storage vessel. Thus, contamination of a gas line, needle valve, or the like, can be avoided. In addition, a liquid level sensor may be provided in the storage vessel for sensing the liquid level of the liquefied gas, so that the gas collection port may be vertically moved within the storage vessel to collect cooled gas close to the liquid level.

13 Claims, 4 Drawing Sheets

COOLING APPARATUS AND SQUID MICROSCOPE USING SAME

BACKGROUND OF THE INVENTION

1. Field of the Invention

This invention relates to apparatus for cooling samples made of various devices and materials (such as various semiconductor devices, semiconductor materials, magnetic materials, superconducting materials, other metal materials or inorganic materials) and maintaining the samples at low temperatures when measurements, observations, or operations are performed regarding such samples at low temperatures reaching the boiling points of liquefied gases.

2. Description of the Related Art

Recently, high-sensitivity magnetometers having spatial resolutions on the order of micrometers and known as SQUIDs (Superconducting Quantum Interference Devices) have been put into practical use, and measurements using SQUID microscopes have been increasingly performed on various devices and materials. Since SQUIDs use superconductivity, it is necessary to cool them at temperatures lower than the temperature of liquid nitrogen (from several K to 77 K). Furthermore, the sample also needs to be retained at low temperatures in many cases. In addition, where samples are observed by tunneling microscopes or atomic force microscopes as well as by SQUIDs, samples are maintained at low temperatures in some cases.

FIG. 2 is a schematic view showing one example of cooling apparatus of related art for cooling a sensor side. A three-axis scanning stage 20, a cooling head 30, a coolant introduction port 42, a sensor 50, a sample 60, etc. are installed inside a vacuum chamber 10. A vacuum pump 70, a liquefied gas storage tank 40, and a transfer tube 90 are installed outside the vacuum chamber 10.

The vacuum chamber 10 is made of stainless steel and maintained in a vacuum state to make provide thermal isolation from the outside.

The three-axis scanning stage 20 is used to place the sample 60 and to control the relative position between the sensor 50 and the sample 60.

The cooling head 30 is a hermetically closed container made from oxygen-free copper to improve the thermal conduction. A first pipe 31 and a second pipe 32 forming an inlet and an outlet for the coolant are connected with the cooling head 30. The flow rate of the coolant flowing into the cooling head 30 is adjusted by a needle valve 33.

The storage vessel is a liquefied gas storage tank 40 which is a vacuum isolation container for storing a liquefied gas 41. Liquid helium is used as the liquefied gas 41.

The coolant introduction port 42 is used to introduce the liquid helium into the cooling head 30 installed inside a vacuum chamber. The coolant introduction port 42 and liquefied gas storage tank 40 are connected by the transfer tube 90, and the coolant stored in the liquefied gas storage tank 40 is introduced into the cooling head 30.

A SQUID having a detection coil about 10 μm in diameter is used as the sensor 50. Niobium operating near the boiling point of liquid helium is used as a superconducting material for fabricating the SQUID. The sensor 50 is made stationary while placed in thermal contact with the cooling head 30.

The vacuum pump 70 is used to lower the pressure inside the second pipe 32, cooling head 30, first pipe 31, and transfer tube 90 and to transfer the liquid helium in the liquefied gas storage tank 40.

The procedure for cooling the cooling head 30 is as follows. The coolant introduction port 42 and liquefied gas storage tank 40 are connected by the transfer tube 90. The vacuum pump 70 is operated and thus the liquid helium stored in the liquefied gas storage tank 40 is passed through the cooling head 30. In this way, the temperature of the cooling head 30 is cooled close to the boiling point of liquid helium.

After cooling of the cooling head 30, the sensor 50 is operated, and the relative position between the sensor 50 and the sample 60 is controlled using the three-axis scanning stage 20. A signal owing to the sensor 50 is recorded. Thus, the magnetic distribution of the sample 60 is measured.

With the above-described cooling apparatus of the related art, where stored liquefied gas is directly used as means for cooling a sensor or a sample to a low temperature, the liquefied gas is often transported into a location to be cooled while using a thin pipe as a medium, or the liquefied gas is transported through a minute space such as a needle valve to adjust the flow rate of the liquefied gas. The stored liquefied gas often contains impurities such as solidified carbon dioxide, oxygen, nitrogen, and water, as well as foreign substances such as microscopic dust and metal fragments. Therefore, foreign substances and impurities sometimes clog up the pipe or needle valve that is a transportation medium for the liquefied gas. Consequently, there is a problem in that the apparatus ceases to function as cooling apparatus. Furthermore, where impurities adhere to the interface portion between the vacuum thermal isolation pipe and coolant introduction port, the interface portion becomes an adhesively bonded state. The vacuum thermal isolation pipe cannot be removed unless an operation for dissolving away the impurities is performed. Hence, the ending operation for the cooling apparatus cannot be performed. Thus, there is a problem in that the workability is poor.

SUMMARY OF THE INVENTION (First Means)

In accordance with the present invention, a gas collection port is provided in a liquefied gas storage tank of a cooling apparatus. Gas produced by evaporation of the liquefied gas is collected and used as a coolant for a cooling head.

(Second Means)

In addition to the first means, a mechanism for measuring the liquid level of the liquefied gas is provided. The gas collection port is made movable vertically.

(Third Means)

In addition to the first means, a gas-cooling mechanism is provided.

(Fourth Means)

In addition to the first means, a structure is provided in which the liquefied gas storage tank is provided with a gas introduction port.

(Fifth Means)

In addition to the first means, a structure is provided in which a refrigerator and a gas introduction port are used instead of the liquefied gas storage tank.

According to the structure of the cooling apparatus owing to the first means, gas evaporated from the liquefied gas is used as a coolant for the cooling head and so even where impurities are mixed in the liquefied gas stored in the liquefied gas storage tank, a high-purity gas can be used as a coolant. Consequently, the pipe or needle valve for transporting the coolant is not clogged up. The cooling apparatus can be run stably.

Owing to the second means, the liquid level of the liquefied gas can be known. Therefore, the gas collection port can be placed close to the liquid level. Gas of lower temperature can be collected and used as a coolant. In consequence, the cooling head can be cooled to a lower temperature.

Owing to the third means, the collected gas becoming the coolant can be cooled to a lower temperature. As a result, the cooling head can be cooled to a lower temperature.

Owing to the fourth means, the pressure inside the liquefied gas storage tank can be adjusted. Therefore, the pressure inside the liquefied gas storage tank can be prevented from becoming a negative pressure. That the gas becoming the coolant cannot be transported can be prevented. Hence, the cooling apparatus can be run stably.

Owing to the fifth means, a high-purity gas can be used as a coolant without using a liquefied gas. Therefore, intrusion of foreign substances into the cooling apparatus can be prevented. The cooling apparatus can be run stably.

DETAILED DESCRIPTION OF THE INVENTION

Embodiments of the present invention are hereinafter described with reference to the drawings.
(Embodiment 1)

Figure 1:
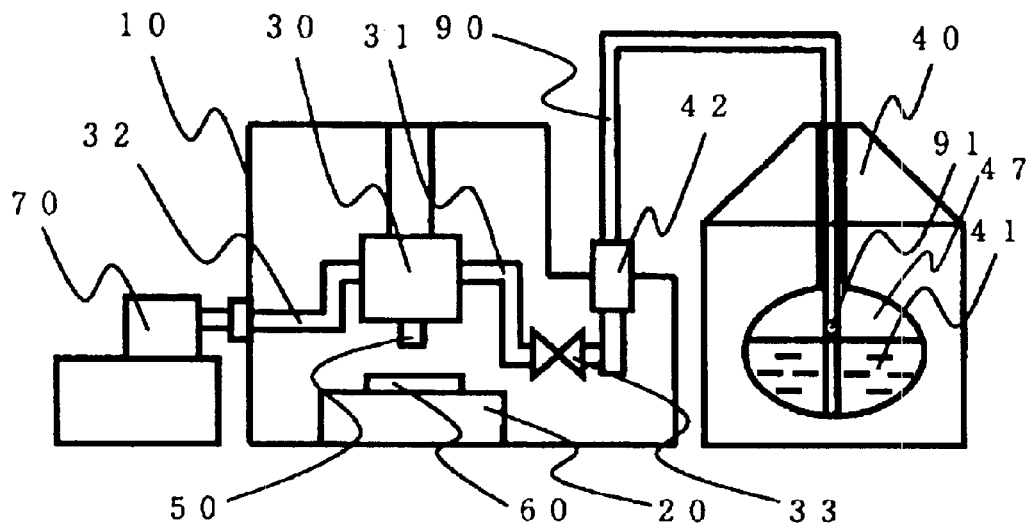
FIG. 1 is a schematic view showing the structure of cooling apparatus showing Embodiment 1 of the present invention.
Figure 2:
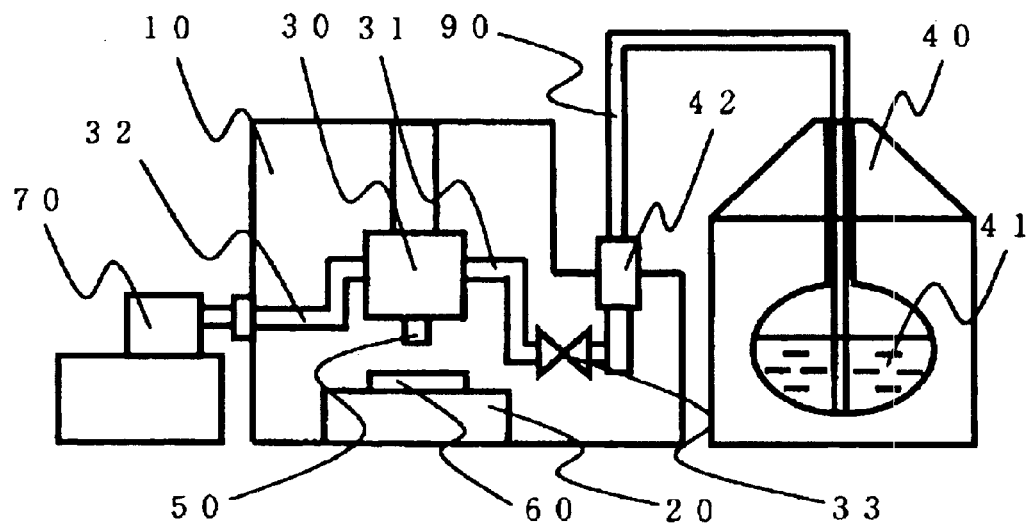
FIG. 2 is a schematic view showing the structure of cooling apparatus of related art.

FIG. 1 is a schematic view showing the structure of cooling apparatus showing Embodiment 1 of the present invention. Cooling apparatus of the invention is used for cooling of a sensor of a SQUID microscope.

A three-axis scanning stage 20, a cooling head 30, a coolant introduction port 42, a sensor 50, a sample 60, etc. are installed inside a vacuum chamber 10. A vacuum pump 70, a liquefied gas storage tank 40, and a transfer tube 90 are installed outside the vacuum chamber 10.

The vacuum chamber 10 is made of stainless steel. The inside is maintained in a vacuum state to provide thermal isolation from the outside.

The three-axis scanning stage 20 is used to place the sample 60 and to control the relative position between the sensor 50 and the sample 60.

The cooling head 30 is a hermetically closed container made from oxygen-free copper to improve the thermal conduction. A first pipe 31 and a second pipe 32 forming inlet and outlet for the coolant are connected with the cooling head 30. The flow rate of the coolant flowing into the cooling head 30 is adjusted by a needle valve 33.

The liquefied gas storage tank 40 is a vacuum thermal isolation container for storing a liquefied gas. Liquid helium is used as the liquefied gas 41. The space over the liquid level of liquid helium inside the liquefied gas storage tank 40 is filled with low-temperature helium gas 47 produced by evaporation of liquid helium.

The transfer tube 90 is used to transfer the coolant held in the liquefied gas storage tank 40 to the cooling head 30. The tube is made up of two flexible tubes (a larger tube and a smaller tube). Vacuum thermal isolation and a radiation thermal shield are provided between the two flexible tubes. With respect to the structure of the transfer tube 90 on the side of the liquefied gas storage tank 40, the front end is closed such that the liquefied gas is not collected. Instead, a gas collection port 91 for collecting helium gas is formed at a position higher than the height of the liquid level of the coolant.

The coolant introduction port 42 is intended to introduce the coolant into the cooling head 30 installed inside the vacuum chamber. The coolant introduction port 42 and liquefied gas storage tank 40 are connected by the transfer tube 90, and the coolant is introduced into the cooling head 30 from the liquefied gas storage tank 40.

A SQUID having a detection coil about 10 $\mu$m in diameter is used as the sensor 50. Niobium operating near the boiling point of liquid helium is used as a superconducting material for fabricating the SQUID. The sensor 50 is made stationary while kept in thermal contact with the cooling head 30.

The vacuum pump 70 is used to lower the pressure inside the second pipe 32, cooling head 30, first pipe 31, and transfer tube 90 and to transfer the liquid helium in the liquefied gas storage tank 40.

The liquefied gas storage tank 40 is a container for transporting and storing liquefied gas that becomes a coolant. At this time, helium is used as the coolant because of the used material of the sensor 50. A container inside the liquefied gas storage tank 40 is filled with liquid helium and helium gas produced by evaporation of the liquid helium.

The procedure for cooling the cooling head 30 is as follows. The coolant introduction port 42 and liquefied gas storage tank 40 are connected by the transfer tube 90. The vacuum pump 70 is operated. Low-temperature helium gas produced by evaporation of the liquid helium inside the liquefied gas storage tank 40 is passed through the cooling head 30 to cool the cooling head 30 close to the boiling temperature of helium.

After cooling of the cooling head 30, the sensor 50 is operated, and the relative position between the sensor 50 and the sample 60 is controlled using the three-axis scanning stage 20. A signal owing to the sensor 50 is recorded. Thus, the magnetic distribution of the sample 60 is measured.
(Embodiment 2)

Figure 3A:
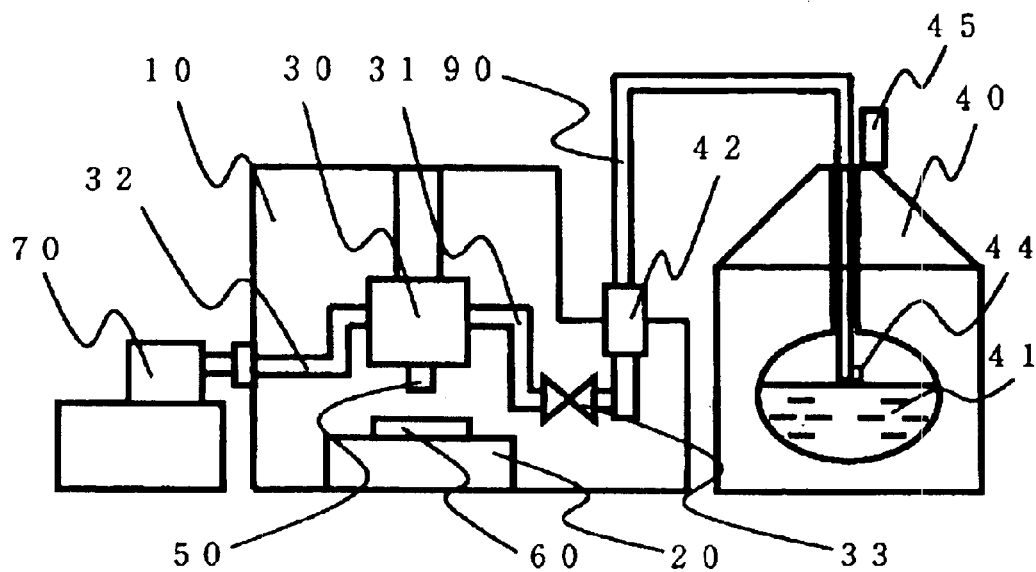
FIG. 3A is a schematic view showing the structure of cooling apparatus showing Embodiment 2 of the invention.

FIG. 3A is a schematic view showing the structure of cooling apparatus showing Embodiment 2 of the invention. This embodiment is by no means different from Embodiment 1 except that the distance between the front end of the transfer tube 90 and the gas collection port 91 is shortened and that a liquid level sensor 44 is fitted to the front end of the transfer tube 90.

Figure 3B:
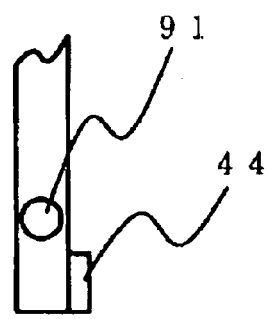
FIG. 3B is a schematic view showing the structure of vicinities of the front end of a transfer tube 90 in Embodiment 2 of the invention.

FIG. 3B is a schematic view showing the structure of vicinities of the front end of the transfer tube 90. The front end of the transfer tube 90 is closed not to collect liquefied gas. The liquid level sensor 44 for judging whether it is inside the coolant or not is fixed. The gas collection port 91 is formed at a position that is several centimeters above the liquid level sensor 44.

The procedure for cooling the cooling head 30 is as follows. The transfer tube 90 is inserted into the liquefied gas storage tank 40. When the liquid level sensor 44 is located at the liquid level of the liquid helium, a Wilson seal port of the liquefied gas storage tank 40 is closed in. The transfer tube is fixed. The vacuum pump 70 is operated. Helium gas close to the liquid level of the liquid helium inside the liquefied gas storage tank 40 is supplied into the cooling head 30, thus cooling it.

After cooling of the cooling head 30, the sensor 50 is operated, and the relative position between the sensor 50 and the sample 60 is controlled using the three-axis scanning stage 20. A signal owing to the sensor 50 is recorded. Thus, the magnetic distribution of the sample 60 is measured.

Since the liquid level in the liquefied gas storage tank 40 drops with the cooling time, the position of the front end of the transfer tube is reset to the liquid level of the liquid helium at appropriate times.

(Embodiment 3)

Figure 4:
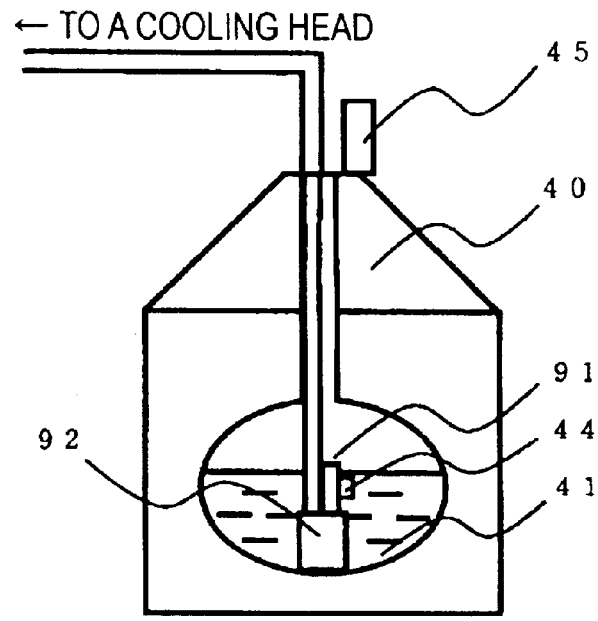
FIG. 4 is a schematic view showing the structure of vicinities of a liquefied gas storage tank 40 of cooling apparatus showing Embodiment 3 of the invention.

FIG. 4 is a schematic view showing the structure of the vicinities of a liquefied gas storage tank 40 of cooling apparatus showing Embodiment 3 of the invention. This embodiment is by no means different from Embodiment 1 except that a gas-cooling mechanism 92 is fitted at the front end of the transfer tube 90 and that a liquid level sensor is mounted at an underpart of the gas collection port 91.

The gas-cooling mechanism 92 is a mechanism for cooling helium gas to the temperature of liquid helium by passing the helium gas through liquid helium once. The gas-cooling mechanism 92 is made up of a pipe for passing helium gas and fins for enhancing the thermal exchange efficiency by increasing the surface area. The material of the gas-cooling mechanism 92 is fabricated using oxygen-free copper at this time. It can be replaced by other material such as aluminum that has good thermal conductivity.

The procedure for cooling the cooling head 30 is as follows. The transfer tube 90 is inserted into the liquefied gas storage tank 40. When the liquid level sensor 44 is located at the liquid level of the liquid helium, the Wilson seal port in the liquefied gas storage tank 40 is closed in. The transfer tube is fixed. The vacuum pump 70 is operated. Thus, helium gas taken in from the gas collection port 91 is cooled to a temperature comparable with the liquid helium temperature by the gas-cooling mechanism 92 and transported to the cooling head 30.

After cooling of the cooling head 30, the sensor 50 is operated, and the relative position between the sensor 50 and the sample 60 is controlled using the three-axis scanning stage 20. A signal owing to the sensor 50 is recorded. Thus, the magnetic distribution of the sample 60 is measured. Since the liquid level in the liquefied gas storage tank 40 drops with the operation time, the position of the front end of the transfer tube is reset to the liquid level of the liquid helium at appropriate times.

(Embodiment 4)

Figure 5:
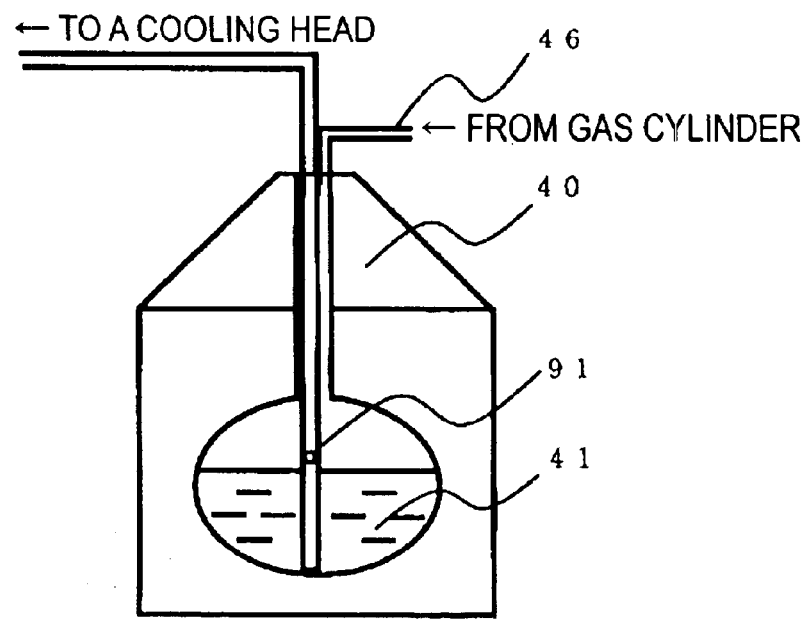
FIG. 5 is a schematic view showing the structure of vicinities of a liquefied gas storage tank 40 of cooling apparatus showing Embodiment 4 of the invention.

FIG. 5 is a schematic view showing the structure of the vicinities of a liquefied gas storage tank 40 of cooling apparatus showing Embodiment 4 of the invention. This embodiment is by no means different from Embodiment 1 except that a gas introduction port 46 for introducing helium gas is formed in an inner-layer container of the liquefied gas storage tank 40.

The gas introduction port 46 is connected with a pipe for helium gas or a helium gas cylinder via a rubber tube and a regulator. The secondary side pressure of the regulator is set to about 0.3 kg f/cm$^2$. Cooling is done while supplying helium gas into the liquefied gas storage tank 40.

(Embodiment 5)

Figure 6:
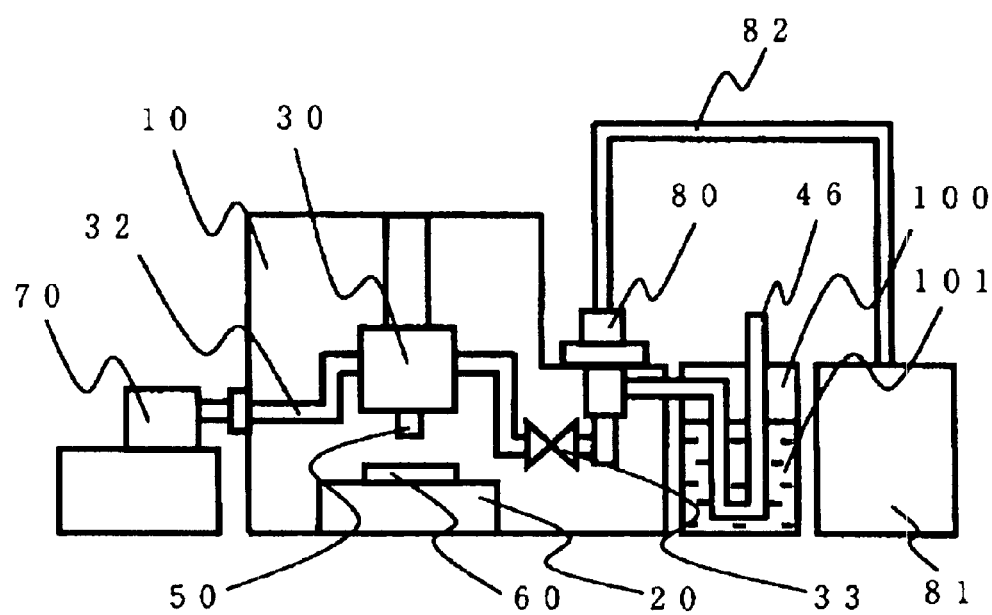
FIG. 6 is a schematic view showing the structure of cooling apparatus showing Embodiment 5 of the invention.

FIG. 6 is a schematic view showing the structure of cooling apparatus showing Embodiment 5 of the invention. Instead of the liquefied gas storage tank and liquid helium in Embodiment 1, the apparatus is so constructed that it uses a refrigerator, helium gas, and a gas precooler.

The gas introduction port 46 is intended to introduce helium gas into the gas precooler 100. The gas introduction port 46 is connected with a helium gas cylinder or helium gas pipe via a rubber tube and a regulator.

The gas precooler 100 is apparatus for cooling ordinary-temperature helium gas introduced from the gas introduction port 46 to a low temperature in the neighborhood of 100 K. At this time, apparatus is used in which piping for thermal exchange is placed in a vacuum vessel for holding liquid nitrogen. The piping for thermal exchange is made up of thin tubes and fins for increasing the surface area. The gas precooler 100 and a refrigerator head 80 are connected by thermal insulation piping.

The refrigerator head 80 is combined with a refrigerator compressor 81 and a flexible hose 82, whereby the head becomes a refrigerator capable of cooling to about 2 K at minimum. Gas piping connected with the gas precooler 100 is installed in the refrigerator head 80 while in thermal contact with it.

The procedure for cooling the cooling head 30 is as follows. The vacuum pump 70 is operated, so that helium gas is introduced into the gas precooler 100 via the gas introduction port 46. The helium gas is cooled to about 77 K to 100 K by the gas precooler 100 and then introduced into the piping in thermal contact with the refrigerator head 80. Thus, the gas is cooled to a low temperature of about 4 K and transported to the cooling head 30, thus cooling the cooling head 30 to a low temperature.

After cooling the cooling head 30, the magnetic distribution of the sample is measured in the same way as in Embodiment 1.

According to the present invention, gas evaporated from liquefied gas is used as a coolant for a cooling head. Therefore, even where impurities are mixed in liquefied gas stored in a liquefied gas storage tank, a gas of high purity can be used as a coolant. Consequently, pipes or needle valve for transporting the coolant is not clogged up. The cooling apparatus can be run stably.

Furthermore, no impurities adhere to the interface portion between vacuum thermal isolation piping and a coolant introduction port. Therefore, the cooling ending operation can be performed without problem. Hence, the workability is improved.

In addition, a gas of a lower temperature can be used. Therefore, the cooling head can be cooled to a lower temperature.

Moreover, the pressure inside the liquefied gas storage tank can be adjusted. Therefore, the pressure inside the liquefied gas storage tank can be prevented from becoming a negative pressure. That the gas becoming a coolant cannot be transported can be prevented. The cooling apparatus can be run stably.

Further, a high-purity gas can be used as a coolant without using a liquefied gas. Consequently, intrusion of foreign substances can be completely prevented. The cooling apparatus can be run quite stably.

According to the present invention, the SQUID microscope can be measure and observe stably.

What is claimed is:

1. A cooling apparatus comprising: a storage vessel for storing a liquefied gas and an evaporated gas produced by evaporation of the liquefied gas; a cooling head cooled by the evaporated gas to approximately a boiling temperature of the liquefied gas; piping for conveying the evaporated gas from the storage vessel to the cooling head; a liquid level sensor provided in the storage vessel for sensing the liquid level of the liquefied gas; and a gas collection port provided at one end portion of the piping above a liquid level of the liquefied gas and being vertically displaceable within the storage vessel for collecting only the evaporated gas from the storage vessel.

2. A cooling apparatus according to claim 1; wherein the piping terminates in a closed end submerged in the liquefied gas at the one end portion, and the gas collection port comprises an opening formed in the piping above the closed end and above the liquid level of the liquefied gas.

3. A cooling apparatus according to claim 1; further comprising a vacuum chamber in which is disposed the cooling head; and a vacuum pump for evacuating the piping to draw the evaporated gas from the storage vessel toward the cooling head.

4. A cooling apparatus according to claim 1; wherein the storage vessel is provided with a gas introduction port for introducing gas therein.

5. A cooling apparatus comprising: a storage vessel for storing a liquefied gas and an evaporated gas produced by evaporation of the liquefied gas; a cooling head cooled by the evaporated gas to approximately a boiling temperature of the liquefied gas; piping for conveying the evaporated gas from the storage vessel to the cooling head; a gas collection port provided at one end portion of the piping above a liquid level of the liquefied gas for collecting only the evaporated gas from the storage vessel; and a gas cooling mechanism proximate the one end portion of the piping and submerged in the liquefied gas for passing the evaporated gas therethrough to cool the evaporated gas.

6. A SQUID microscope comprising: a cooling apparatus according to claim 1; a sample stage for supporting a sample; and a SQUID mounted to the cooling head.

7. A cooling apparatus comprising: a gas introduction port for introducing a gas; a precooler connected to the gas introduction port and containing a liquefied gas for cooling the gas; a refrigerator having a compressor for refrigerating the cooled gas; a cooling head cooled by the refrigerated gas; and piping for conveying the refrigerated gas from the refrigerator to the cooling head.

8. A cooling apparatus according to claim 7; further comprising a vacuum chamber in which is disposed the cooling head; and a vacuum pump for evacuating the piping to draw the evaporated gas from the refrigerator toward the cooling head.

9. A SQUID microscope comprising: a cooling apparatus according to claim 7; a sample stage for supporting a sample; and a SQUID mounted to the cooling head.

10. A SQUID microscope comprising: a vacuum chamber; a sample stage for supporting a sample in the vacuum chamber; a cooling head provided in the vacuum chamber; a SQUID mounted to the cooling head; a storage vessel for storing a liquefied gas and an evaporated gas produced by evaporation of the liquified gas; piping for conveying the evaporated gas from the storage vessel to the cooling head; a gas collection port provided at one end portion of the piping above a liquid level of the liquefied gas for collecting only the evaporated gas from the storage vessel; and a gas cooling mechanism proximate the one end portion of the piping and submerged in the liquefied gas for passing the evaporated gas therethrough to cool the evaporated gas.

11. A SQUID microscope according to claim 10; further comprising a vacuum pump for evacuating the piping to draw the evaporated gas from the storage vessel toward the cooling head.

12. A SQUID microscope comprising: a vacuum chamber; a sample stage for supporting a sample in the vacuum chamber; a cooling head provided in the vacuum chamber; a SQUID mounted to the cooling head; a storage vessel for storing a liquefied gas and an evaporated gas produced by evaporation of the liquified gas; piping for conveying the evaporated gas from the storage vessel to the cooling head; a gas collection port provided at one end portion of the piping above a liquid level of the liquefied gas for collecting only the evaporated gas from the storage vessel; and a liquid level sensor provided in the storage vessel for sensing the liquid level of the liquefied gas; wherein the gas collection port is vertically displaceable within the storage vessel.

13. A SQUID microscope according to claim 10; wherein the storage vessel is provided with a gas introduction port for introducing a gas therein.

\* \* \* \* \*